US010710072B2

(12) United States Patent
Hong et al.

(10) Patent No.: US 10,710,072 B2
(45) Date of Patent: Jul. 14, 2020

(54) PARTICLE SEPARATION APPARATUS AND PARTICLE SEPARATION METHOD (71) Applicant: EXOZUM INC., Seoul (KR)

(72) Inventors: Jong Wook Hong, Seoul (KR); Soo Jeong Shin, Seoul (KR); Sung Hoon Kim, Seoul (KR); Min Chul Park, Gyeonggi-do (KR); Dae Young Han, Gyeonggi-do (KR)

(73) Assignee: EXOZUM INC., Seoul (KR)

( * ) Notice: Subject to any disclaimer, the term of this patent is extended or adjusted under 35 U.S.C. 154(b) by 54 days.

(21) Appl. No.: 16/073,135

(22) PCT Filed: Jan. 25, 2017

(86) PCT No.: PCT/KR2017/000918
§ 371 (c)(1),
(2) Date: Jul. 26, 2018

(87) PCT Pub. No.: WO2017/131452
PCT Pub. Date: Aug. 3, 2017

(65) Prior Publication Data
US 2019/0030534 A1    Jan. 31, 2019

(30) Foreign Application Priority Data

Jan. 26, 2016  (KR) ........................ 10-2016-0009559

(51) Int. Cl.
*B07C 5/36*      (2006.01)
*B01L 3/00*      (2006.01)
(Continued)

(52) U.S. Cl.
CPC .......... *B01L 3/502753* (2013.01); *B01L 3/00* (2013.01); *C12Q 1/68* (2013.01); *G01N 1/40* (2013.01);
(Continued)

(58) Field of Classification Search
CPC ................. G01N 15/02; G01N 1/4094; G01N 2015/0288; G01N 2015/1081;
(Continued)

(56) References Cited

U.S. PATENT DOCUMENTS 8,387,803 B2 * 3/2013 Thorslund ......... B01L 3/502761
                                                              209/552
9,588,100 B2 * 3/2017 Appleyard ......... G01N 21/6486
(Continued)

FOREIGN PATENT DOCUMENTS

JP    2006-263693 A    10/2006
JP    2012-239449 A    10/2012
(Continued)

OTHER PUBLICATIONS

International Search Report and Written Opinion in corresponding PCT Application No. PCT/KR2017/000918, dated May 8, 2017.
(Continued)

*Primary Examiner* — Joseph C Rodriguez
(74) *Attorney, Agent, or Firm* — Leason Ellis LLP (57) ABSTRACT A particle separation apparatus, according to an embodiment of the present invention, may comprise: a first input flow path into which a first fluid containing a plurality of particles of different sizes is introduced; a second input flow path into which a second fluid not containing particles is introduced; a connection flow path and the second input flow path so that a third fluid in which the first fluid and the second fluid are mixed movies; a plurality of discharge flow paths where the plurality of particles which come out through the other end of the connection flow path are separated and discharged according to the size of the particles; and a branch flow path where at least a part of the third fluid which comes out through the other end of the connection flow path is discharged.

20 Claims, 5 Drawing Sheets (51) Int. Cl.
*C12Q 1/68* (2018.01)
*G01N 1/40* (2006.01)
*G01N 15/02* (2006.01)

(52) U.S. Cl.
CPC ...... *G01N 15/02* (2013.01); *B01L 2200/0652* (2013.01); *B01L 2200/10* (2013.01); *B01L 2300/0864* (2013.01); *B01L 2400/00* (2013.01); *G01N 2015/0288* (2013.01)

(58) Field of Classification Search
CPC ...... G01N 2015/1087; G01N 2015/149; B01L 2200/027; B01L 2200/0636; B01L 2200/0652; B01L 2200/10; B01L 2400/0436; B07C 5/02; B07C 5/04; B07C 5/34; B07C 5/36
See application file for complete search history.

(56) References Cited

U.S. PATENT DOCUMENTS

| | | | | |
|---|---|---|---|---|
| 9,757,726 | B2 * | 9/2017 | Sharpe | B01L 3/502761 |
| 9,770,721 | B2 * | 9/2017 | Chiou | G01N 15/0656 |
| 9,789,235 | B2 * | 10/2017 | Gifford | A61M 1/3693 |
| 10,228,381 | B2 * | 3/2019 | Levner | B01L 3/502761 |
| 2009/0042310 | A1 * | 2/2009 | Ward | G01N 15/1404 436/154 |
| 2009/0226994 | A1 * | 9/2009 | Lemor | B01L 3/502715 435/173.1 |
| 2010/0126922 | A1 * | 5/2010 | Takahashi | B01D 21/283 210/201 |
| 2010/0139377 | A1 * | 6/2010 | Huang | C02F 1/76 73/61.75 |
| 2014/0008307 | A1 * | 1/2014 | Guldiken | B01L 3/502761 210/748.05 |
| 2014/0231315 | A1 * | 8/2014 | Laurell | G01N 33/5005 209/18 |
| 2019/0168221 | A1 * | 6/2019 | Sollier | B01L 3/502738 |

FOREIGN PATENT DOCUMENTS

| | | |
|---|---|---|
| KR | 10-1138904 B1 | 5/2012 |
| KR | 10-2012-0113533 A | 10/2012 |

OTHER PUBLICATIONS

Steigert, J. et al., "Rapid Prototyping of Microfluidic Chips in COC," Journal of Micromechanics and Microengineering 2007, vol. 17, No. 2, pp. 333-341.

* cited by examiner

[Figure 7: Panels labeled 0%, 50%, 70%, 80%, 90%, 90%]

FIG. 8

(1) 1st Fluid:2nd Fluid = 5:95

1  2  3  4  5  6  7  8  9

(2) 1st Fluid:2nd Fluid = 10:90

1  2  3  4  5  6  7  8  9

(3) 1st Fluid:2nd Fluid = 1:99

PARTICLE SEPARATION APPARATUS AND PARTICLE SEPARATION METHOD

CROSS-REFERENCE TO RELATED PATENT APPLICATIONS

This application is a U.S. National Phase Application under 35 U.S.C. § 371 of International Patent Application No. PCT/KR2017/000918, filed Jan. 25, 2017 that claims priority to KR 10-2016-0009559, filed Jan. 26, 2016, all of which are incorporated by reference in their entireties. The International Application was published on Aug. 3, 2017 as International Publication No. WO 2017/131452.

The present invention relates to a particle separation apparatus and a particle separating method.

BACKGROUND OF THE INVENTION

In recent years, there is a growing demand for a micro-scale system such as a lab-on-a-chip as the demand for diagnosis and synthesis using a small amount of materials increases. Techniques to isolate and control small amounts of material are particularly important in the medical, chemical, and biological fields.

A lab-on-a-chip refers to a laboratory on a chip or a laboratory in a chip, and it is used to make micro-channels of less than nanoliters on a substrate made mainly of glass, polymer resin or silicone, and it has been developed to carry out the existing experiment or research process quickly by moving a liquid sample of several nanometers through the microchannel.

Particle separation systems based on such lab-on-a-chip technology are being studied. Conventional particle separation systems, however, have complex structures and complex separation mechanisms, and have low separation accuracy.

In addition, the structure of particles separated by the particle separation system may be disturbed, resulting in loss of function after separation.

DETAILED DESCRIPTION OF THE INVENTION

Technical Problem

On the basis of the technical background as described above, the present invention aims to provide a particle separating apparatus in which a plurality of particles are not damaged during the separation process.

Technical Solution

A particle separation apparatus according to an embodiment of the present invention may comprise:

a first input flow path through which a first fluid containing a plurality of particles of different sizes is introduced;

a second input flow path through which a second fluid not containing particles is introduced;

a connection flow path through which a third fluid moves, wherein one end of the connection flow path is connected to the first input flow path and the second input flow path so that the first fluid and the second fluid are mixed to form the third fluid;

a plurality of discharge flow paths through which the plurality of particles coming out of the other end of the connection flow path are separated and discharged according to the size of the particle; and a branch flow path through which at least a portion of the third fluid coming out of the other end of the connection flow path is discharged.

According to an embodiment of the present invention, the connection flow path may comprise:

a substrate;

a first side surface which is formed on the substrate and is connected to the first input flow path; and a first side surface surface which faces the first side surface on the substrate and is connected to the second input flow path.

According to an embodiment of the present invention, the plurality of particles may slidingly move to the first side surface.

According to another embodiment of the present invention, the first side surface is inclined toward the second side surface with respect to the substrate.

According to another embodiment of the present invention, the angle formed between the first side surface and the substrate may be less than 90 degrees.

According to another embodiment of the present invention, the first side surface is in a flat plane shape.

According to still another embodiment of the present invention, the first side surface may be in a stair shape.

According to still another embodiment of the present invention, the second side surface may be inclined toward the first side surface with respect to the substrate.

According to still another embodiment of the present invention, the angle between the second side surface and the substrate may be less than 90 degrees.

According to further another embodiment of the present invention, the plurality of discharge flow paths may be spaced apart from each other in a direction crossing the flow direction of the third fluid on the other end of the connection flow path.

According to further another embodiment of the present invention, the intervals between a pair of adjacent discharge flow paths among the plurality of discharge flow paths may be equal to each other.

According to further another embodiment of the present invention, the flow rate ratio of the first fluid to the second fluid introduced into the first input flow path and the second flow path may be in a range of 0.1:99.9 to 50:50.

According to still further another embodiment of the present invention, the flow rate of the third fluid discharged through the branch flow path may be adjustable.

According to still further another embodiment of the present invention, the flow rate of the third fluid discharged through the branch flow path may be in a range of 70% to 95% of the third fluid coming out of the connection flow path.

According to still further another embodiment of the present invention, the second input flow path may be inclined at a pre-determined angle with respect to the first input flow path.

According to still further another embodiment of the present invention, the plurality of particles may be nanoparticles.

According to further another embodiment of the present invention, the plurality of particles may be organelles.

According to still further another embodiment of the present invention, the first and second fluids may comprise any one of organic solvent selected from the group consisting of polyetheramine, hexane, and toluene; distilled water; aqueous solution containing tween 20; saline solution; culture medium; and PBS (Phosphate Buffer Saline), respectively.

According to still further another embodiment of the present invention, the apparatus may be applied to any one of a blood analysis chip, a DNA array, and a microsensor.

A method for separating particles according to another embodiment of the present invention may comprise:

Introducing a first fluid containing a plurality of particles having different particle sizes into a first input flow path;

Introducing a second fluid not containing particles into a second input flow path;

passing the first fluid and the second fluid through a connection flow path which is connected to outlet parts of the first input flow path and the second input flow path;

passing the plurality of particles, which have passed through the connection flow path, through each of the plurality of discharge flow paths according to a particle size; and passing at least a portion of a third fluid through a branch flow path located at the outlet part of the connection flow path, wherein the first fluid and the second fluid, which have passed through the connection flow path, are mixed to form the third fluid.

According to another embodiment of the present invention, the connection flow path may comprise:

a substrate;

a first side surface which is formed on the substrate and is connected to the first input flow path; and a second side surface which faces the first side surface on the substrate and is connected to the second input flow path.

According to another embodiment of the present invention, the first side surface is inclined toward the second side surface with respect to the substrate.

According to another embodiment of the present invention, the angle formed between the first side surface and the substrate may be less than 90 degrees.

According to still another embodiment of the present invention, the flow rate ratio of the first fluid to the second fluid introduced into the first input flow path and the second flow path may be in a range of 0.1:99.9 to 50:50.

According to still another embodiment of the present invention, the flow rate of the third fluid discharged through the branch flow path may be adjustable.

According to still further another embodiment of the present invention, the flow rate of the third fluid discharged through the branch flow path may be in a range of 70% to 95% of the third fluid coming out of the connection flow path.

Advantageous Effect

According to the particle separating apparatus and the particle separating method described above, particles having different sizes can be separated by particle size. According to the particle separating apparatus and the particle separating method according to this example, the microparticles and the nanoparticles can be separated from each other, and the nanoparticles having different sizes can be separated from each other.

In addition, the use of physical, chemical and electrical energy is minimized to prevent particles from being damaged during the separation of the particles.

In addition, the particle separating apparatus and the particle separating method of the present example can separate nanoparticles such as separation of semiconductor nanoparticles, separation of bio-nanoparticles, blood, umbilical cord blood, exosomes, and fine dusts.

MODE FOR CARRYING OUT INVENTION

Hereinafter, examples of the present invention will be described in detail with reference to the accompanying drawings, which will be readily apparent to those skilled in the art to which the present invention pertains. The present invention may be embodied in many different forms and is not limited to the examples described herein. In order to clearly illustrate the present invention, parts not related to the description are omitted, and the same or similar components are denoted by the same reference numerals throughout the specification.

In addition, the size and thickness of each component shown in the drawings are arbitrarily shown for convenience of explanation, and thus the present invention is not necessarily limited to those shown in the drawings.

In the drawings, the thicknesses are enlarged to clearly indicate layers and regions. In the drawings, for the convenience of explanation, the thicknesses of some layers and regions are exaggerated. When a portion such as a layer, film, region, or plate is referred to as being "on" or "above" another portion, it also includes the case where there is another portion in the middle as well as the other portion.

Also, throughout the specification, when an element is referred to as "including" an element, it means that the element may include other elements as well, without departing from the other elements unless specifically stated otherwise. Also, throughout the specification, the term "on" refers to be located above or below a target portion, and does not necessarily mean that the target portion is located on the above side with respect to the gravitational direction.

Hereinafter, a particle separator according to an example of the present invention will be described with reference to FIGS. 1 to 3.

Figure 1:
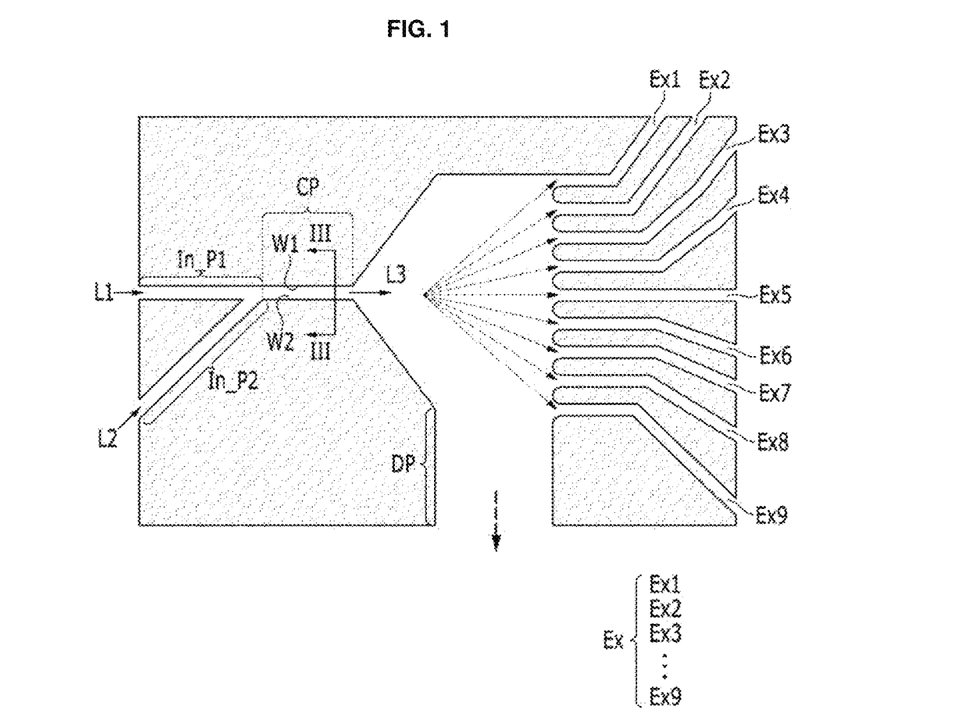
FIG. 1 is a top plan view of a particle separating apparatus according to an example of the present invention.

FIG. 1 is a top plan view of a particle separator according to an example of the present invention. FIG. 2 is a drawing for explaining a process of separating particles passing through a connection flow path. FIG. 3 is a cross-sectional view of the connection flow path cut along the line III-III in FIG. 1.

Figure 2:
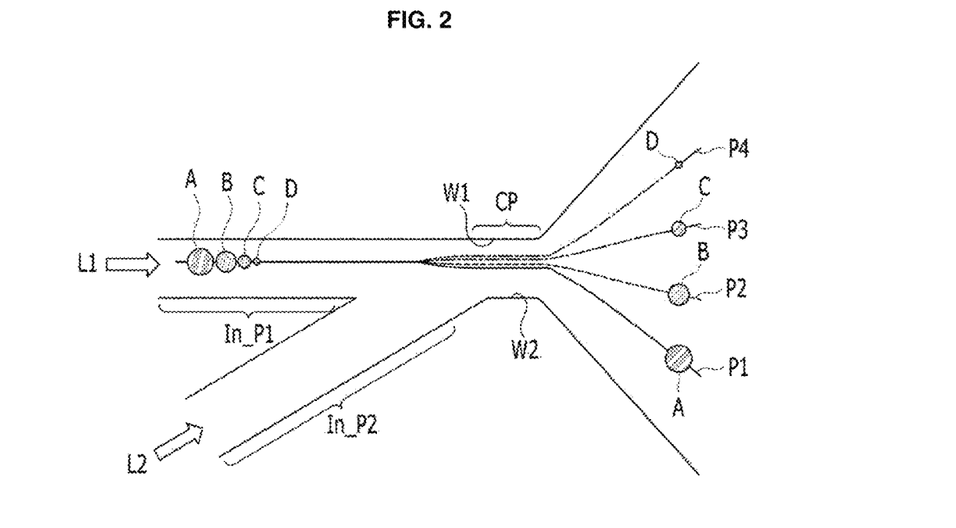
FIG. 2 is a drawing illustrating a process of separating particles passing through a connection flow path.
Figure 3:
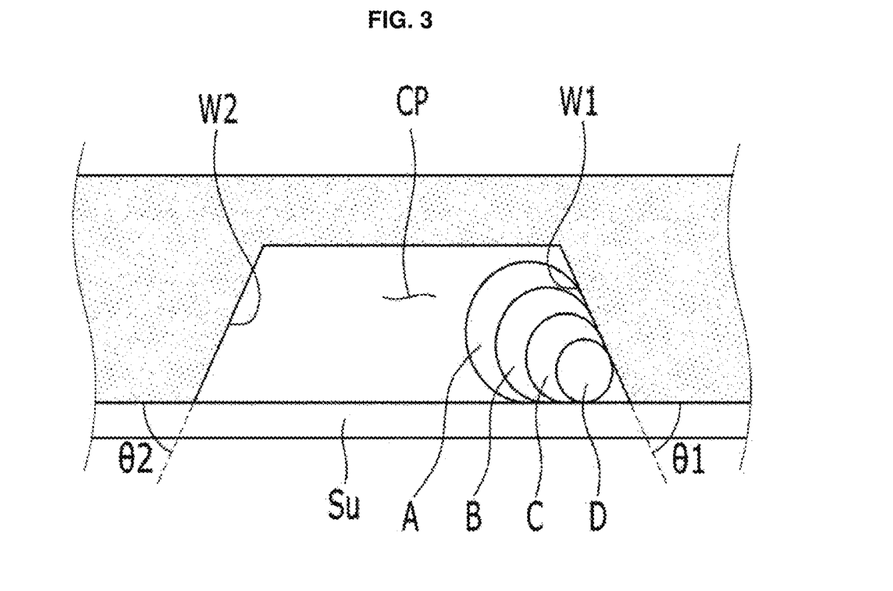
FIG. 3 is a cross-sectional view of the connection flow path cut along the line in FIG. 1.

Referring to FIGS. 1 to 3, a particle separating apparatus according to an embodiment of the present invention comprises a first input flow path (In_P1), a second input flow path (In_P2), a connection flow path (CP), a plurality of discharge flow paths (EX1 to EX9) and a branch flow path (DP). According to this example, the plurality of particles (A, B, C, and D) having passed through the connection flow path (CP) connected to the first and second input flow paths (In_P1 and In_P2) are separated and discharged into a plurality of discharge flow path (Ex) depending on the size of the particles. At this time, a part of the fluid that flows out through the connection flow path (CP) flows out to the outside through the branch flow path (DP), and the flow rate of the fluid flowing out of the branch flow path (DP) through the branch flow path (DP) can be controlled so that the plurality of particles are separated by the plurality of discharge flow paths (Ex) by the particle size.

Referring to FIG. 1, a first fluid (L1) is injected through a first input flow path (In_P1). At this time, the first fluid (L1) contains a plurality of particles having different sizes. That is, the first fluid (L1) containing a plurality of particles is injected through the input flow path (In_P1). The plurality of particles introduced through the first input flow path (In_P1) may be separated from each other by the particle size through the particle separator according to the present example.

At this time, the plurality of particles may be nanoparticles, a quantum dot, or an organelle. Herein, the nanoparticles mean particles having a particle size of several nanometers. Particles to be applied to the particle separation apparatus according to the present example may be various particles having a size of several nanometers.

On the other hand, quantum dots represent nanometer sized semiconductor crystals produced through chemical synthesis processes. At this time, the quantum dot can emit light of various colors by generating a light wavelength of different length depending on the particle size without changing the kind of the material. And, the second fluid (L2), which does not contain particles, is introduced into the second input flow path (In_P2). Unlike the first fluid (L1) described above, the second fluid (L2) consists solely of liquid.

That is, the first input flow path (In_P1) and the second input flow path (In_P2) are disposed at the inlet side of the particle separator according to the present example. At this time, a plurality of particles of different sizes to be separated are introduced into one input flow path, that is, the first input flow path (In_P1) through the first fluid (L1), and the second fluid (L2), which does not contain particles, is injected into the other input flow path, that is, the second input flow path (In_P2).

At this time, the first fluid (L1) and the second fluid (L2) may any one of organic solvent selected from the group consisting of polyetheramine, hexane, and toluene; distilled water; aqueous solution containing tween 20; saline solution; culture medium; and PBS (Phosphate Buffer Saline); respectively. For example, in the present example, a plurality of particles having different sizes may be included in the culture medium to be introduced into the first input flow path (In_P1). The first input flow path (In_P1) and the second input flow path (In_P2) are connected to the connection flow path (CP). As shown in FIG. 1, the first input flow path (In_P1) and the second input flow path (In_P2) are connected to one end of the connection flow path (CP).

At this time, the first input flow path (In_P1) and the second input flow path (In_P2) form an angle with each other and are connected to one end of the connection channel (CP). The first input flow path (In_P1) and the second input flow path (In_P2) are arranged parallel to each other and are not connected to one end of the connection flow path (CP). That is, the second input flow path (In_P2) is inclined at a certain angle based on the first input flow path (In_P1) and is connected to the connection flow path (CP).

For example, as shown in FIG. 1, the first input flow path (In_P1) is arranged in parallel with the connection flow path (CP), and the second input flow path (In_P2) is disposed at a certain angle.

Referring to FIG. 2, when the first input flow path (In_P1) and the second input flow path (In_P2) form a certain angle with respect to each other, a plurality of particles contained in the first fluid (L1) can be moved along the first side (W1) of the connection path (CP). Here, the first side (W1) represents one side of the connection flow path (CP) connected to the first input flow path (In_P1).

For example, it is assumed that the first fluid (L1) includes a plurality of particles (A, B, C, and D) having different sizes. The first fluid L1 having passed through the first connection flow path (In_P1) slides on the first side (W1) of the connection flow path (CP) by the second fluid (L2) and moves along the connection flow path (CP).

At a point where the first input path (In_P1) and the second input path (In_P2) meet, the plurality of particles (A, B, C, D) of the first fluid (L1) move toward the first side of the connection path (CP) by the second fluid (L2) of the second input path (In_P2). This is because the second fluid (L2) injected into the connection flow path (CP) is inclined at a certain angle with respect to the first fluid (L1). That is, the plurality of particles (A, B, C, and D) flowing into the connection flow path (CP) are moved while sliding on the first side surface (W1) of the connection flow path CP by the second fluid (L2).

According to this example, as shown in FIG. 3, the first side surface (W1) of the connection flow path (CP) is arranged to be inclined at a first angle ($\theta 1$) 1 with respect to the substrate (Su). At this time, the first side surface (W1) is inclined toward the second side surface (W2) facing the first side surface (W1). Here, the second side surface (W2) represents one side of the connection flow path (CP) connected to the second input flow path (In_P2).

Figure 4:
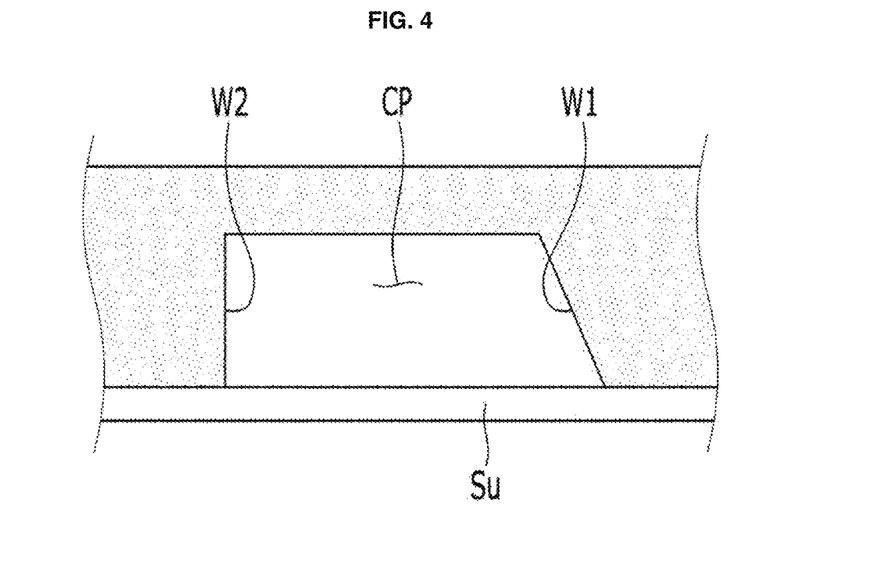
FIG. 4 is a first modified example of the connection flow path of FIG. 3.

Further, the second side surface (W2) may be inclined at the second angle ($\theta 2$) with respect to the substrate (Su). However, the present invention is not limited thereto, and the second side surface (W2) may be disposed perpendicular to the substrate (Su), as shown in the first modification of FIG. 4. This is because the plurality of particles (A, B, C and D) moves along with the first side surface (W1) by the second fluid (L2) and do not move along with the second side surface (W2).

At this time, the first angle ($\theta 1$) and the second angle ($\theta 2$) may be less than 90°. Preferably, the first angle ($\theta 1$) and the second angle ($\theta 2$) may be between 35° to 55°. When the first side surface (W1) is inclined at the first angle ($\theta 1$), the particles contained in the first fluid (W1) may be spaced from the first side surface (W1) in the particle size order.

Referring to FIG. 3, the plurality of particles (A, B, C, and D) is spaced from the first side surface (W1) in the order of particle size. For example, the particles (A), the particles (B), the particles (C), and the particles (D), in the order of larger particle size, are spaced from the first side surface (W1). Hereinafter, for convenience, it is assumed that the particles (A, B, C and D) are spherical and the particle size is determined by the diameter of the particles (A, B, C and D). As a result, the particle size (A), the particle (B), the particle (C) and the particle (D) in the order of larger particle size are spaced apart from the first side surface (W1).

According to this example, since the first side surface (W1) is inclined toward the second side surface (W2), it is possible to increase the distance between the particles (A, B, C and D), as compared to the case where the first side surface (W1) is not inclined and is disposed perpendicular to the substrate (Su). Here, the distance between the particles (A, B, C and D) means the distance between the centers of the particles (A, B, C and D). As a result, the particles (A, B, C, and D) passing through the connection flow path (CP) can be separated from each other according to the particle size, and can introduced into the plurality of discharge flow paths (EX1 to EX9). A detailed description thereof will be described below.

At this time, the first side surface (W1) may have the shape of flat plane. As shown FIG. 3, the first side surface (W1) is formed in a flat plane shape, and the plurality of particles (A, B, C, and D) are attached to the substrate (Su) and the first side surface (W1) that is in a flat plane shape to be located in the connection flow path (CP).

Figure 5:
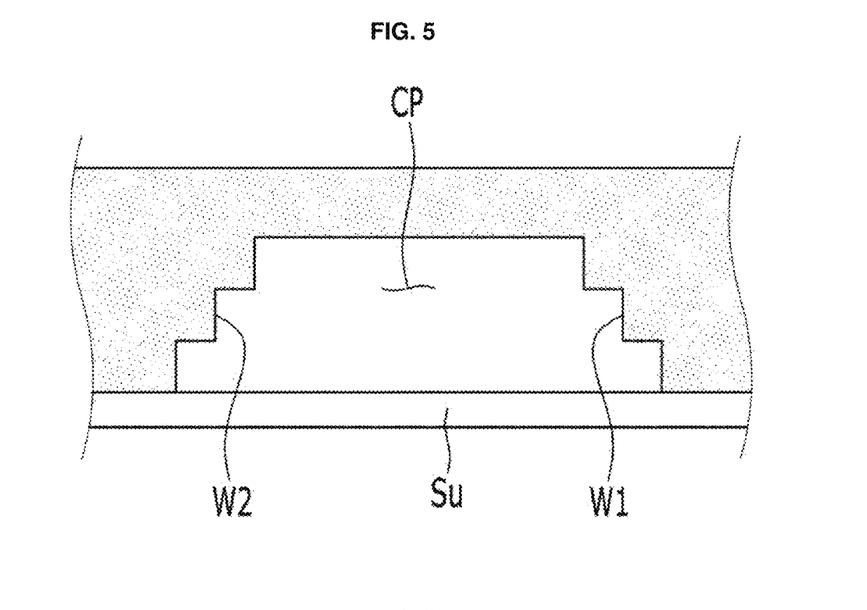
FIG. 5 is a second modified example of the connection flow path of FIG. 3.
Figure 6:
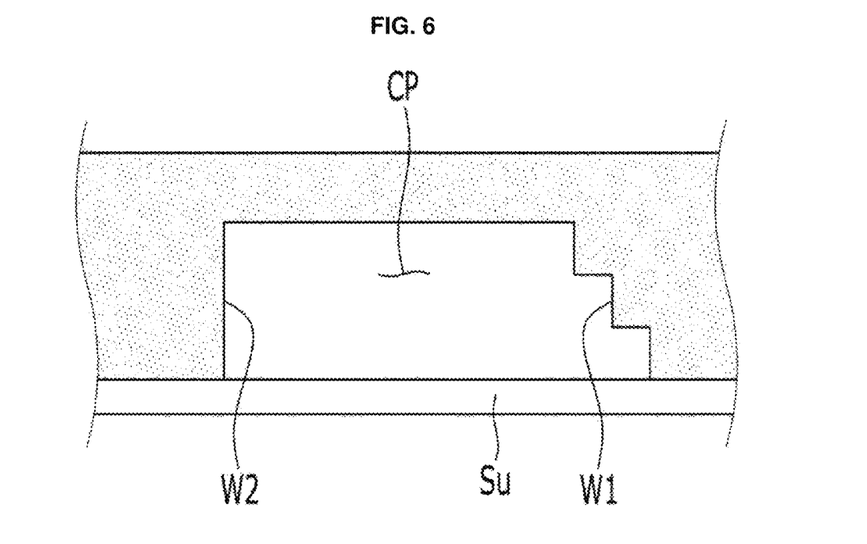
FIG. 6 is a third modified example of the connection flow path of FIG. 3.

On the other hand, the first side surface (W1) may have the shape of stairs as shown in the second modification of FIG. 5. When the first side surface (W1) is formed in the shape of stairs, the distance between the plurality of particles (A, B, C, and D) can be further increased than the shape of flat plate is formed. At this time, as shown in FIG. 5, the second side surface (W2) may also have the shape of stairs as the first side surface (W1).

Referring again to FIGS. 1 and 2, the plurality of particles (A, B, C, and D) are contained in the third fluid (L3) in which the first fluid (L1) and the second fluid (L2) are mixed to pass through the flow path (CP). As described above, the plurality of particles (A, B, C, and D) move while sliding on the first side surface (W1). Then, when passing through the connection path (CP), they move separately from one another according to the particle size as shown in FIG. 2.

In FIG. 2, the plurality of particles (A, B, C, and D) is sliding along the first side surface (W1) by the second fluid (L2), and moves obliquely toward the first side surface (W1) when passing through the connecting flow path (CP) by inertial force.

At this time, the particles (A, B, C, and D) move along with different paths depending on the size of the particles. More specifically, the plurality of particles A, B, C, and D move along with the paths P1, P2, P3, and P4, respectively. That is, the particles (A) move along with the path (P1), the particles (B) move along with the path (P2), the particles (C) move along with the path (P3) and the particles (D) move along with the path (P4), respectively.

As shown in FIG. 2, the smaller the particle size, the more it is bent toward the first side surface (W1). Therefore, the particles (D), particles (C), particles (B) and particles (A) in the order of small particle size are greatly bent toward the first side surface (W1).

On the other hand, according to the present example, when the first side surface (W1) is inclined toward the second side surface (W2) as described above, the distance between the particles (A, B, C and D) is increased and thereby, the distance between the paths (P1, P2, P3, and P4) through which the particles (A, B, C, and D) that have passed through the connection flow path (CP) move, increases. As the distance between a pair of adjacent paths of the paths (P1, P2, P3, and P4) is increased, particles moving along with the path can be easily separated.

For example, when the particles (A) moving along the path (P1) and the particles (B) moving along the path (P2) are observed, the distance between the path (P1) and the path P2 is further increased when the first side surface W1 is tilted as compared with the case where the first side surface (W1) is not inclined. This is because the first side surface (W1) is inclined so that the distance between the particle (A) and the particle (B) in the connection flow path (CP) is increased.

Referring again to FIG. 1, a plurality of discharge flow path (Ex) is arranged at the other end of the connection flow path (CP). The plurality of discharge flow path (Ex) can separate and discharge a plurality of particles discharged through the connection flow path (CP) according to the size of the particles.

For example, a plurality of discharge flow paths (Ex1, Ex2, Ex3, Ex4, Ex5, Ex6, Ex7, Ex8, and Ex9) can be formed at the other end of the connection flow path (CP). Although it is described that nine discharge flow paths are arranged in FIG. 1, the number of discharge flow paths is not limited thereto, and may be less than nine or more. According to this example, it can be separated and discharged respectively by a plurality of discharge flow paths (Ex1, Ex2, Ex3, Ex4, Ex5, Ex6, Ex7, Ex8, and Ex9) according to the size of the particles.

At this time, a this time, the plurality of discharge channels (Ex1, Ex2, Ex3, Ex4, Ex5, Ex6, Ex7, Ex8, and Ex9) may be arranged in a direction crossing the flow direction of the third fluid (L3) coming out from the connection channel (CP). In other words, the plurality of discharge flow paths (Ex1, Ex2, Ex3, Ex4, Ex5, Ex6, Ex7, Ex8, and Ex9) can be spaced apart from each other in a direction crossing the flow direction.

According to the present example, the plurality of discharge flaw paths (Ex1, Ex2, Ex3, Ex4, Ex5, Ex6, Ex7, Ex8, and Ex9) are arranged at the same intervals in the cross direction. More specifically, the intervals between the adjacent pair of the discharge flow paths of the plurality of discharge flow paths (Ex1, Ex2, Ex3, Ex4, Ex5, Ex6, Ex7, Ex8, and Ex9) are equal to each other. For example, the interval between the discharge flow path (Ex1) and the discharge flow path (Ex2) and the interval between the discharge flow path (Ex2) and the discharge flow path (Ex3) are equal to each other. Similarly, the interval between the discharge flow path (Ex2) and the discharge flow path (Ex3) and the interval between the discharge flow path (Ex3) and the discharge flow path (Ex4) are equal to each other.

On the other hand, according to the present example, a branch flow path (DP) through which at least a part of the third fluid (L3) coming out through the connection flow path (CP) is discharged is disposed. The branch flow path (DP) is located on the outlet side of the connection flow path (CP) and is disposed adjacent to the plurality of discharge flow path (Ex).

At this time, the branch flow path (DP) discharges a portion of the third fluid (L3) to the outside, and a plurality of particles are separated and discharged at a plurality of discharge flow path (Ex) corresponding to each particle size. When the branch flow path (DP) discharges a portion of the third fluid (L3) to the outside, the distance between the paths in which the above-mentioned particles move can be increased. As a result, particles of different sizes can be easily separated by particle size.

According to the present example, the flow rate of the third fluid (L3) discharged through the branch flow path DP can be adjusted. By controlling the flow rate of the third fluid (L3) discharged through the branch flow path (DP), it is possible to more easily separate and discharge the plurality of particles discharged through the connection flow path (CP) according to the particle size.

Figure 7:
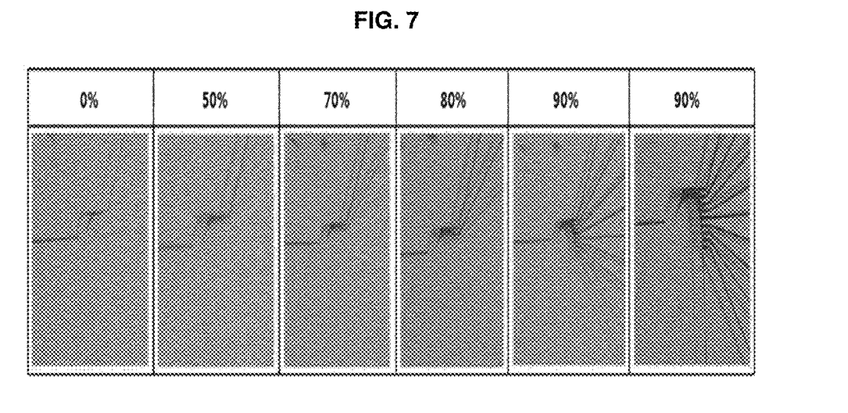
FIG. 7 is a view showing the degree of particle separation according to a change in the flow rate of the branch flow path.

FIG. 7 is a graph showing the degree of separation of particles according to a change in the flow rate of the branch flow path. It can be seen that particles are easily separated when the flow rate of the third fluid coming out through the branch flow path (DP) is higher than a certain ratio with respect to the third fluid flowing through the connection flow path (CP).

Referring to FIG. 7, when the ratio of the flow rate of the third fluid flowing out through the branch flow path (DP) is increased, the discharge flow path (Ex) through which the third fluid coming out through the connection flow path (CP) flows out is increased. Here, the percentage (%) shown in FIG. 7 represents the ratio of the third fluid discharged through the branch flow path (DP) for the third fluid coming out through the connection flow path CP. The path shown in red in FIG. 7 represents a path through which the third fluid discharged through the connection flow path (CP) moves.

For example, when the flow rate discharged to the branch flow path (DP) is 0% of the connection flow path (CP), that is, when there is no flow rate coming out through the branch flow path (DP), the third fluid is discharged along one discharge flow path (Ex). On the other hand, when the ratio (%) of the flow rate discharged to the branch flow path (DP) is increased, it can be seen that the number of the discharge flow paths (Ex), which is the path through which the third fluid is discharged, increases. Particularly, when the flow rate discharged to the branch flow path (DP) is 70% to 95% of the connection flow path (CP), the number of the discharge flow paths (Ex), which is the path through which the third fluid is discharged, becomes the maximum.

According to the present example, the flow rates of the first fluid (L1) and the second fluid (L2) flowing into the first input flow path (In_P1) and the second input flow path (In_P2) are different from each other. Particularly, when the flow rate ratio of the first fluid (L1) and the second fluid (L2) is 0.1:99.9 to 50:50, the plurality of particles coming out through the connection flow path (CP) can be easily separated and discharged. More preferably, when the flow rate ratio of the first fluid (L1) and the second fluid (L2) is 5:95, the plurality of particles can be easily separated by the size of the particles through the plurality of discharge flow paths.

Figure 8:
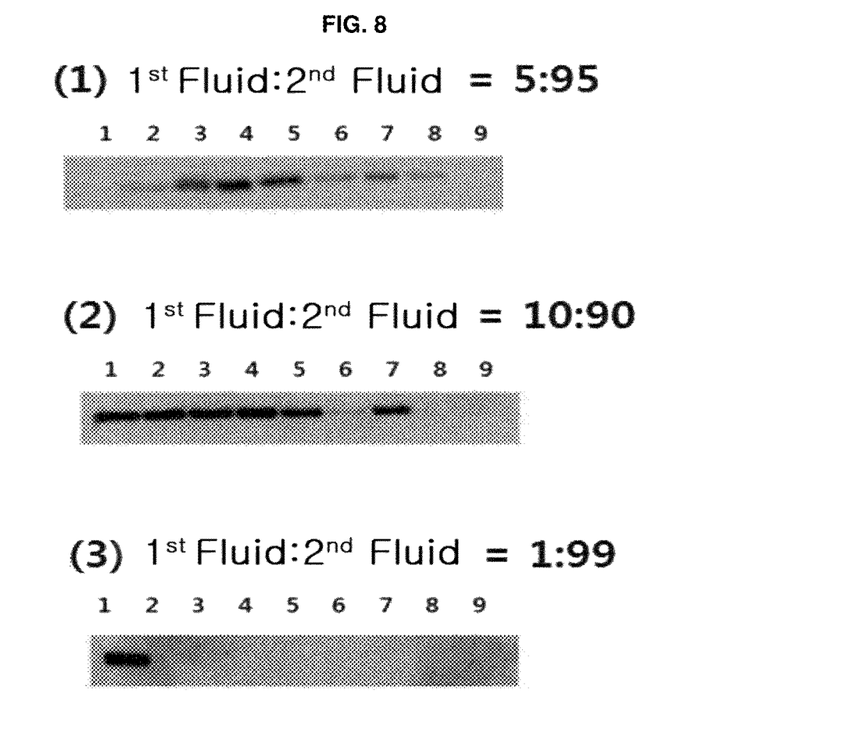
FIG. 8 is a view showing the degree of particle separation according to the flow rate change of the first and second input flow paths FIG.

FIG. 8 is a diagram showing the degree of particle separation due to a flow rate change of the first and second input flow paths. FIG. 8 is an experimental result showing the degree of separation and discharge into a plurality of discharge flow path (Ex1, Ex2, Ex3, Ex4, Ex5, Ex6, Ex7, Ex8, and Ex9) of the particle separating apparatus according to the present example according to the relative change of the flow rate passing through the first input flow path (In_P1) and the second input flow path (In_P2). The results of the experiment of FIG. 8 were performed using Exosome and Syntenin was used as a marker of exosomes.

On the other hand, a Western blotting method was used to detect exosomes located in a plurality of discharge flow path (Ex1, Ex2, Ex3, Ex5, Ex6, Ex7, Ex8 and Ex9). In this experiment, a syringe pump was used to inject fluid into the first input flow path (In_P1) and the second input flow path (In_P2).

Referring to FIG. 8(1), when the flow rate of the second fluid (L2) containing no particles is larger than the flow rate of the first fluid (L1) containing the particles, for example, Exosomes are not evenly detected in the plurality of discharge flow paths (Ex1 Ex2, Ex3, Ex4, Ex5, Ex6, Ex7, Ex8 and Ex9) when the flow rate of the flow rate of the second fluid (L2) is 1:99.

On the other hand, when the flow rate of the first fluid (L1) and the flow rate ratio of the second fluid (L2) are 5:95 or 10:90, the exosomes were evenly detected in each of the plurality of discharge flow paths (Ex1, Ex2, Ex3, Ex4, Ex5, Ex6, Ex7, Ex8, and Ex9).

In particular, as described above, when the flow rate ratio of the first fluid (L1) and the second fluid (L2) is 5:95, it can be seen that the exosomes are uniformly separated into the plurality of discharge flow paths (Ex1, Ex2, Ex3, Ex4, Ex5, Ex6, Ex7, Ex8, and Ex9).

FIG. 8 is an experimental result that it is confirmed that the third fluid flows out to each of the plurality of discharge flow paths (Ex1, Ex2, Ex3, Ex4, Ex5, Ex6, Ex7, Ex8, and Ex9) by controlling the flow ratio of the first fluid (L1) and the second fluid (L2).

Figure 9:
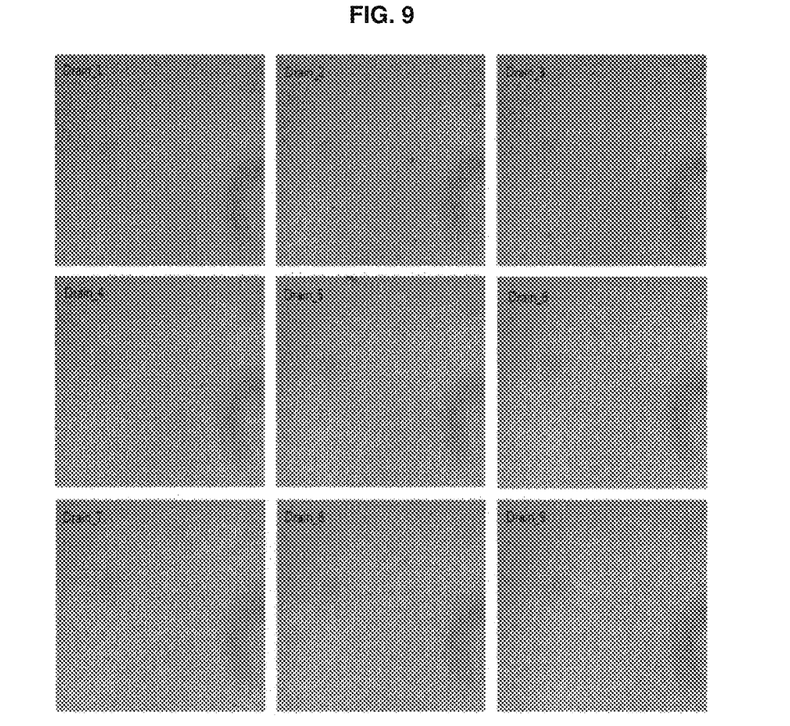
FIG. 9 is a view showing a result of separation of particles through the discharge flow path.

FIG. 9 is a view showing a result of separation of particles through the discharge flow path.

FIG. 9 is the result of the separation using the particle separating apparatus according to the present example after mixing 1 μm and 10 μm polystyrene particles in a weight ratio of 18:1. In this experiment, the particles were mixed with distilled water or distilled water mixed with tween 20. It was performed under the condition that the flow ratio of the first fluid (L1) to the second fluid (L2) was 5:95 and the flow rate of the fluid discharged through the branch flow path (DP) was 70% of the connection flow path (CP). An optical microscope was used to identify polystyrene particles in the discharge flow path.

Referring to FIG. 9, 1 μm polystyrene particles having small particle sizes were mainly detected in the front discharge flow path, and 10 μm polystyrene particles having large particle sizes were mainly detected in the rear discharge flow path. The front discharge flow path means that the number of discharge flow path is small (for example, Ex1, Ex2, Ex3, and Ex4) and the rear discharge flow path means that the number of discharge flow path is large (for example, Ex5, Ex6, Ex7, Ex8, and Ex9). Drain_1, Drain_2, etc. shown in the photograph of FIG. 9 correspond to discharge flow paths Ex1, Ex2, etc., respectively.

Figure 10:
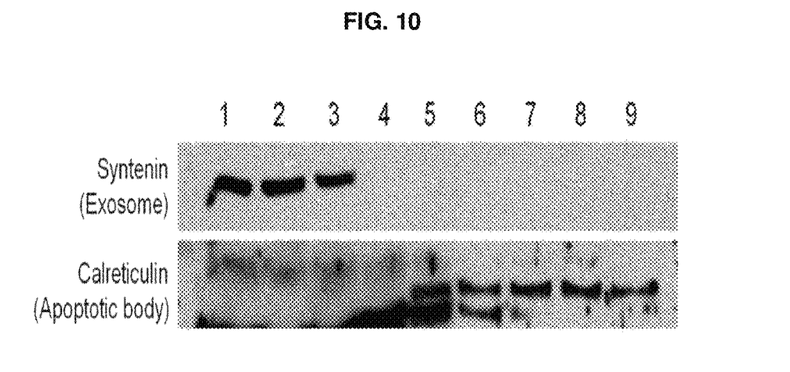
FIG. 10 is a result of separating an exosome and an apoptotic body using the particle separating apparatus according to the present example.

FIG. 10 is a result of separating an exosome and an apoptotic body using the particle separating apparatus according to the present example.

FIG. 10 is a graph showing the results of separating a fluid mixture of an exosome having a particle size of about 100 nm to 200 nm and an apoptotic body having a particle size of about 1 μm to 5 μm using a particle separating apparatus according to the present embodiment.

In this experiment, exosomes and apoptotic bodies were mixed in a culture medium or PBS (Phosphate Buffer Saline), and the mixture was injected into the input flow path. The flow ratio of the first fluid (L1) to the second fluid (L2) was 10:90, it was performed under the condition that the flow rate discharged to the branch flow path (DP) was 75% of the connection flow path (CP). A Western blotting method was used to detect particles located in a plurality of discharge flow paths (Ex1, Ex2, Ex3, Ex4, Ex5, Ex6, Ex7, Ex8, and Ex9). Syntenin was used as a marker of exosomes, and calreticulin was used as a marker of apoptotic bodies.

Similarly to FIG. 9, in FIG. 10, exosomes having small particle sizes were mainly detected in the front discharge flow path, and apoptotic bodies having large particle sizes were mainly detected in the rear exit flow path. Here, the front discharge flow path means that the number of discharge flow path is small (for example, Ex1, Ex2, Ex3, and Ex4), and the rear discharge flow path means that the number of discharge flow path is large (for example, Ex5, Ex6, Ex7, Ex8, and Ex9).

Hereinafter, a particle separation method according to an example of the present invention will be described. In explaining the particle separation method of the present example, detailed description of the same configuration as the particle separation apparatus described above will be omitted.

Referring to FIG. 1, first fluid (L1) is introduced into a first input flow path (In_P1). At this time, the first fluid (L1) includes a plurality of particles having different sizes to be separated by the particle size. That is, the first fluid (L1) containing a plurality of particles is introduced through the first input flow path (In_P1).

Meanwhile, the second fluid (L2) containing no particles is introduced into the second input flow path (In_P2). Unlike the first fluid (L1) described above, the second fluid (L2) consists solely of liquid.

That is, according to the present example, the first fluid (L1) containing particles and the second fluid (L2) containing no particles are injected into different input flow paths (In_P1) and (In_P2). At this time, the first fluid (L1) and the second fluid (L2) may be simultaneously introduced.

At this time, the first input flow path (In_P1) and the second input flow path (In_P2) form a certain angle with each other and are combined to the inlet of the connection channel CP. The first input flow path (In_P1) and the second input flow path (In_P2) are arranged parallel to each other and are not combined to one end of the connection channel CP. That is, the second input flow path (In_P2) is inclined at a predetermined angle with respect to the first input flow path (In_P1) and is combined to the connection flow path (CP).

For example, as shown in FIG. 1, the first input flow path (In_P1) is arranged parallel to the connection flow path (CP), and the second input flow path In_P2 may be disposed at a certain angle with respect to the first input flow path (In_P2).

On the other hand, according to the present example, the flow rates of the first fluid (L1) and the second fluid (L2) flowing into the first input flow path (In_P1) and the second input flow path (In_P2) are different from each other. Particularly, when the flow rate ratio of the first fluid (L1) and the second fluid (L2) is 0.1:99.9 to 50:50, the plurality of particles coming out through the connection flow path (CP) can be easily separated and discharged. More preferably, when the flow rate ratio of the first fluid L1 and the second fluid L2 is 5:95, the plurality of particles can be easily separated by the size of the particles through the plurality of discharge flow paths.

Next, after the first fluid (L1) and the second fluid (L2) are introduced, respectively, the first fluid (L1) and the second fluid (L2) flows into the connection flow path (CP) after passing through the first input flow path (_P1) and the second input flow path (In_P2).

Referring to FIG. 2, when the first input flow path (In_P1) and the second input flow path (In_P2) form a certain angle with respect to each other, a plurality of particles contained in the first fluid (L1) can be moved along with the first side surface (W1) of the connection flow path (CP). Here, the first side surface (W1) represents one side of the connection flow path (CP) connected to the first input flow path In_P1).

For example, it is assumed that the first fluid (L1) includes a plurality of particles (A, B, C, and D) having different sizes. The first fluid (L1) having passed through the first connection passage (In_P1) slides on the first side surface (W1) of the connection passage CP by the second fluid (L2) and moves along with the connection passage (CP).

At a point where the first input channel (In_P1) and the second input channel (In_P2) meet, the plurality of particles (A, B, C, D) of the first fluid (L1) move toward the first side surface (W1) of the connection path (CP) by the second fluid (L2) of the second input flow path (In_P2). This is because the second fluid (L2) introduced into the connection flow path (CP) is inclined at a certain angle with respect to the first fluid (L1). That is, the plurality of particles (A, B, C, and D) flowing into the connection flow path (CP) are moved while sliding on the first side surface (W1) of the connection flow path (CP) by the second fluid (L2).

As described above, the first side surface (W1) of the connection flow path (CP) is arranged to be inclined at a first angle ($\theta 1$) with respect to the substrate (Su), as shown in FIG. 3. At this time, the first side surface W1 is inclined toward the second side surface (W2) facing the first side surface (W1). Here, the second side surface (W2) represents one side of the connection flow path (CP) connected to the second input flow path (In_P2).

Further, the second side surface (W2) may is arranged to be inclined at a first angle ($\theta 2$) with respect to the substrate Su. However, the present invention is not limited thereto, and the second side surface (W2) may be disposed perpendicular to the substrate Su, as shown in the first modification of FIG. 3. This is because the plurality of particles (A, B, C and D) moves along with the first side surface (W1) by the second fluid (L2) and do not move along with the second side surface (W2).

At this time, the first angle ($\theta 1$) and the second angle ($\theta 2$) may be less than 90°. Preferably, the first angle ($\theta 1$) and the second angle ($\theta 2$) may be between 35° to 55°. When the first side surface (W1) is inclined at the first angle ($\theta 1$), the particles contained in the first fluid (W1) may be spaced from the first side surface (W1) in the particle size order.

More specifically, the plurality of particles (A, B, C, and D) is spaced from the first side surface (W1) in the order of particle size. For example, the particles (A), the particles (B), the particles (C), and the particles (D), in the order of larger particle size, are spaced from the first side surface (W1). For convenience, it is assumed that the particles (A, B, C and D) are spherical and the particle size is determined by the diameter of the particles (A, B, C and D). As a result, the particles (A), the particles (B), the particles (C) and the particles (D) in the order of larger particle size are spaced apart from the first side surface (W1).

According to the present example, since the first side surface (W1) is inclined toward the second side surface (W2), it is possible to increase the distance between the particles (A, B, C and D), as compared to the case where the first side surface (W1) is not inclined and is disposed perpendicular to the substrate (Su). Here, the distance between the particles (A, B, C and D) means the distance between the centers of the particles (A, B, C and D).

Next, the particles (A, B, C, and D) passing through the connection flow path (CP) can be separated from each other according to the particle size, and can introduced into the plurality of discharge flow paths (EX1 to EX9). At this time, a plurality of discharge flow path (Ex) is arranged at the other end of the connection flow path (CP). The plurality of discharge flow path (Ex) can separate and discharge a plurality of particles discharged through the connection flow path (CP) according to the size of the particles.

As described above, a plurality of discharge flow paths (Ex1, Ex2, Ex3, Ex4, Ex5, Ex6, Ex7, Ex8, and Ex9) can be formed at the other end of the connection flow path (CP). Although it is described that nine discharge flow paths are arranged in FIG. 1, the number of discharge flow paths is not limited thereto, and may be less than nine or more. According to this example, it can be separated and discharged respectively by a plurality of discharge flow paths (Ex1, Ex2, Ex3, Ex4, Ex5, Ex6, Ex7, Ex8, and Ex9) according to the size of the particles.

According to the present example, at least a portion of the third fluid (L3) discharged through the connection flow path (CP) is passed through the branch flow path (DP). The branch flow path (DP) is located on the outlet part of the connection flow path (CP) and is disposed adjacent to the plurality of discharge flow path (Ex).

The branch flow path (DP) discharges a portion of the third fluid (L3) to the outside so that a plurality of particles are separated and discharged into a plurality of discharge flow paths Ex corresponding to each particle size. When the branch flow path (DP) discharges a portion of the third fluid (L3) to the outside, the distance between the paths in which the above-mentioned particles move can be increased. As a result, particles of different sizes can be easily separated by particle size.

According to the present example, the flow rate of the third fluid (L3) discharged through the branch flow path (DP) can be adjusted. By controlling the flow rate of the third fluid (L3) discharged through the branch flow path (DP), it is possible to more easily separate and discharge the plurality of particles discharged through the connection flow path (CP) according to the particle size.

The flow rate of the third fluid (L3) discharged through the branch flow path (DP) can be adjusted. By controlling the flow rate of the third fluid (L3) discharged through the branch flow path (DP), it is possible to more easily separate and discharge the plurality of particles discharged through the connection flow path (CP) according to the particle size.

For example, when the flow rate discharged to the branch flow path (DP) is 0% of the connection flow path (CP), that is, when there is no flow rate coming out through the branch flow path (DP), the third fluid is discharged along one discharge flow path (Ex). On the other hand, when the ratio (%) of the flow rate discharged to the branch flow path (DP) is increased, it can be seen that the number of the discharge flow paths (Ex), which is the path through which the third fluid is discharged, increases. Particularly, when the flow rate discharged to the branch flow path (DP) is 70% to 95% of the connection flow path (CP), the number of the discharge flow paths (Ex), which is the path through which the third fluid is discharged, becomes the maximum. In the particle separating device and the particle separating method according to the example of the present invention, the branch flow path (DP) for discharging a part of the fluid flowing out through the connection flow path (CP) is disposed at the outlet side of the connection flow path (CP), and the plurality of particles discharged through the connection flow path (CP) can be easily separated by the particle size.

According to the particle separating apparatus and the particle separating method of the present example, the microparticles and the nanoparticles can be separated from each other, and the nanoparticles having different sizes can be separated from each other.

In addition, the present example can be applied to a non-destructive high-efficiency exosome precision separation system, a blood analysis chip, a DNA array, a microsensor, or a precision separation system.

In addition, the present example can be applied to a non-destructive high-efficiency exosome precision separation system, a blood analysis chip, a DNA array, a microsensor, or a precision separation system.

As described above, while the present invention has been particularly shown and described with reference to exemplary examples and figures, the present invention is not limited thereto. It will be understood by those skilled in the art that various modifications and changed are possible in the technical idea of the present invention and within the scope of equivalents of the claims described below.

What is claimed is:

1. A particle separation apparatus, the apparatus comprising:
    a first input flow path through which a first fluid containing a plurality of particles of different sizes is introduced;
    a second input flow path through which a second fluid not containing particles is introduced;
    a connection flow path through which a third fluid moves, wherein one end of the connection flow path is connected to the first input flow path and the second input flow path so that the first fluid and the second fluid are mixed to form the third fluid;
    a plurality of discharge flow paths through which the plurality of particles coming out of the other end of the connection flow path are separated and discharged according to the size of the particle; and
    a branch flow path through which a portion of the third fluid coming out of the other end of the connection flow path is discharged externally,
    wherein the particles comprise nanoparticles,
    wherein a plurality of discharge flow paths are spaced apart from each other in a direction crossing the flow direction of the third fluid on the other end of the connection flow path,
    wherein the branch flow path is arranged in a direction crossing the flow direction of the third fluid on the other end of the connection flow path, and is configured to adjust the flow rate of the third fluid which is discharged externally through the branch flow path so as to increase a distance between paths in which each of the plurality of particles coming out of the other end of the connection flow path moves,
    wherein the connection flow path comprises a substrate; a first side surface which is formed on the substrate and is connected to the first input flow path; and a second side surface which faces the first side surface on the substrate and is connected to the second input flow path,
    wherein the first side surface is inclined toward the second side surface with respect to the substrate at an angle formed between the first side surface and the substrate which is between 35 degrees and 55 degrees.

2. The apparatus of claim 1, wherein the plurality of particles slidingly move to the first side surface.

3. The apparatus of claim 1, wherein the first side surface is in a flat plane shape.

4. The apparatus of claim 1, wherein the first side surface is in a stair shape.

5. The apparatus of claim 1, wherein the second side surface is inclined toward the first side surface with respect to the substrate.

6. The apparatus of claim 5, wherein the angle between the second side surface and the substrate is less than 90 degrees.

7. The apparatus of claim 1, wherein the intervals between a pair of adjacent discharge flow paths among the plurality of discharge flow paths is equal to each other.

8. The apparatus of claim 1, wherein the first input flow path and the second flow path are configured to introduce the first fluid and the second fluid, respectively, in a flow rate ratio of the first fluid to the second fluid which is in a range of 0.1:99.9 to 50:50.

9. The apparatus of claim 1, wherein the flow rate of the third fluid discharged through the branch flow path is adjustable.

10. The apparatus of claim 1, wherein the branch flow path (DP) is configured to discharge the third fluid at a flow rate which is in a range of 70% to 95% of the third fluid coming out of the connection flow path.

11. The apparatus of claim 1, wherein the second input flow path is inclined at a pre-determined angle with respect to the first input flow path.

12. The apparatus of claim 1, wherein the plurality of particles are organelles.

13. The apparatus of claim 1, wherein the plurality of particles are quantum dots.

14. The apparatus of claim 1, wherein the first and second fluids comprises any one of organic solvent selected from the group consisting of polyetheramine, hexane, and toluene; distilled water; aqueous solution containing tween 20; saline solution; culture medium; and PBS (Phosphate Buffer Saline), respectively.

15. The apparatus of claim 1, wherein the apparatus is applied to any one of a blood analysis chip, a DNA array, and a microsensor.

16. A method for separating particles, the method comprising:
introducing a first fluid containing a plurality of particles having different particle sizes into a first input flow path;
introducing a second fluid not containing particles into a second input flow path;
passing the first fluid and the second fluid through a connection flow path which is connected to outlet parts of the first input flow path and the second input flow path;
separating the plurality of particles, which have passed through the connection flow path, through each of a plurality of discharge flow paths according to a particle size; and
discharging externally a portion of a third fluid through a branch flow path located at the outlet part of the connection flow path, wherein the first fluid and the second fluid, which have passed through the connection flow path, are mixed to form the third fluid,
wherein the particles comprise nanoparticles,
wherein the plurality of discharge flow paths are spaced apart from each other in a direction crossing the flow direction of the connection flow path,
wherein the branch flow path is arranged in a direction crossing the flow direction of the connection flow path,
wherein the step of passing the first fluid and the second fluid through the connection flow path comprises spacing the plurality of particles from the side surfaces of the connecting flow path in the order of a particle size by an angle formed at the side surfaces of the connecting flow path,
wherein the step of discharging externally a portion of a third fluid through the branch flow path comprises adjusting a flow rate of the third fluid discharged through the branch flow path which is in a range of 70% to 95% of the third fluid coming out of the connection flow path.

17. The method of claim 16, wherein the connection flow path comprises
a substrate;
a first side surface which is formed on the substrate and is connected to the first input flow path; and
a second side surface which faces the first side surface on the substrate and is connected to the second input flow path.

18. The method of claim 17, wherein the first side surface is inclined toward the second side surface with respect to the substrate.

19. The method of claim 18, wherein the angle formed between the first side surface and the substrate is less than 90 degrees.

20. The method of claim 16, wherein the first input flow path and the second flow path are configured to introduce the first fluid and the second fluid, respectively, in a flow rate ratio of the first fluid to the second fluid which is in a range of 0.1:99.9 to 50:50.

* * * * *